US012406370B2

(12) United States Patent
DiCarlo et al.

(10) Patent No.: US 12,406,370 B2
(45) Date of Patent: *Sep. 2, 2025

(54) DETERMINING CHROMOPHORE CONCENTRATIONS IN TISSUES

(71) Applicant: Intuitive Surgical Operations, Inc., Sunnyvale, CA (US)

(72) Inventors: Jeffrey M. DiCarlo, Austin, TX (US); Ian E. McDowall, Woodside, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/650,707

(22) Filed: Apr. 30, 2024

(65) Prior Publication Data
US 2024/0281975 A1    Aug. 22, 2024

Related U.S. Application Data

(63) Continuation of application No. 17/311,300, filed as application No. PCT/US2019/064542 on Dec. 4, 2019, now Pat. No. 12,002,208.
(Continued)

(51) Int. Cl.
*G06T 7/00* (2017.01)

(52) U.S. Cl.
CPC .. *G06T 7/0014* (2013.01); *G06T 2207/10064* (2013.01); *G06T 2207/10068* (2013.01)

(58) Field of Classification Search
CPC .................................................. G06T 7/0014
See application file for complete search history.

(56) References Cited

U.S. PATENT DOCUMENTS

| 10,395,652 B2 | 8/2019 | Chen et al. |
| 12,002,208 B2 * | 6/2024 | DiCarlo ................ G06T 7/0014 |

(Continued)

FOREIGN PATENT DOCUMENTS

| CN | 1489446 A | 4/2004 |
| CN | 102860809 A | 1/2013 |

(Continued)

OTHER PUBLICATIONS

Extended European Search Report for Application No. EP24183903.4, mailed on Oct. 14, 2024, 08 pages.

(Continued)

*Primary Examiner* — Kevin Ky

(57) ABSTRACT

Technology described herein can be embodied in a method that includes obtaining, using an imaging device, a plurality of images of a surgical scene, each image in the plurality of images being obtained under illumination by electromagnetic radiation in one of a plurality of wavelength ranges. The plurality of wavelength ranges are at least partially non-overlapping. The method also includes identifying a set of pixel values across multiple images in the plurality of images, wherein each pixel value in the set of pixel values is substantially representative of a particular portion of the surgical scene and determining, based on the set of pixel values and a chromophore model, a concentration of a chromophore in the particular portion of the surgical scene, wherein the chromophore model represents relationships between combinations of pixel values and chromophore concentrations.

20 Claims, 9 Drawing Sheets

Related U.S. Application Data

(60) Provisional application No. 62/775,463, filed on Dec. 5, 2018.

(56) References Cited

U.S. PATENT DOCUMENTS

| | | | |
|---|---|---|---|
| 2007/0024946 A1* | 2/2007 | Panasyuk | A61B 5/416 |
| | | | 359/253 |
| 2010/0198027 A1* | 8/2010 | Dixon | A61B 5/412 |
| | | | 600/323 |
| 2013/0210156 A1* | 8/2013 | Wooley | G01N 21/75 |
| | | | 436/63 |
| 2013/0286176 A1 | 10/2013 | Westwick et al. | |
| 2013/0345541 A1* | 12/2013 | Nau, Jr. | A61B 18/24 |
| | | | 600/407 |
| 2014/0016132 A1* | 1/2014 | Schmitz | A61B 5/14551 |
| | | | 356/337 |
| 2014/0378843 A1* | 12/2014 | Valdes | A61B 1/063 |
| | | | 600/476 |
| 2015/0054930 A1* | 2/2015 | Bangera | G06V 20/693 |
| | | | 348/77 |
| 2016/0374562 A1* | 12/2016 | Vertikov | A61B 5/0095 |
| | | | 600/424 |
| 2018/0339073 A1* | 11/2018 | Clynne | A61L 2/0047 |
| 2019/0320875 A1* | 10/2019 | Jones | G06T 7/0012 |
| 2022/0015617 A1 | 1/2022 | DiCarlo et al. | |
| 2024/0024051 A1* | 1/2024 | Tokarchuk | A61B 34/00 |
| 2024/0281975 A1* | 8/2024 | DiCarlo | A61B 1/0638 |

FOREIGN PATENT DOCUMENTS

| | | |
|---|---|---|
| EP | 2452610 A1 | 5/2012 |
| EP | 2891450 A1 | 7/2015 |
| JP | 2013013560 A | 1/2013 |
| JP | 2016511015 A | 4/2016 |
| WO | WO-2011004801 A1 | 1/2011 |
| WO | WO-2013115323 A1 | 8/2013 |
| WO | WO-2015023990 A1 | 2/2015 |
| WO | WO-2015093104 A1 | 6/2015 |
| WO | WO-2016100214 A1 | 6/2016 |
| WO | WO-2017154292 A1 | 9/2017 |
| WO | WO-2017216585 A1 | 12/2017 |
| WO | WO-2018043728 A1 | 3/2018 |
| WO | WO-2018070474 A1 | 4/2018 |
| WO | WO-2018159083 A1 | 9/2018 |

OTHER PUBLICATIONS

International Preliminary Report on Patentability for Application No. PCT/US2019/064542, mailed on Jun. 17, 2021, 10 pages.

International Search Report and Written Opinion for Application No. PCT/US2019/064542, mailed Mar. 25, 2020, 18 pages.

Office Action for Chinese Application No. CN20198079965, mailed Nov. 6, 2023, 31 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

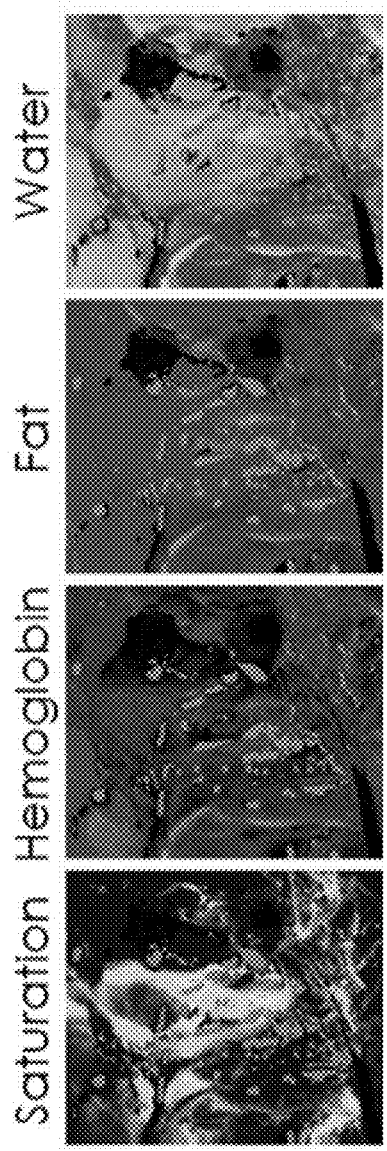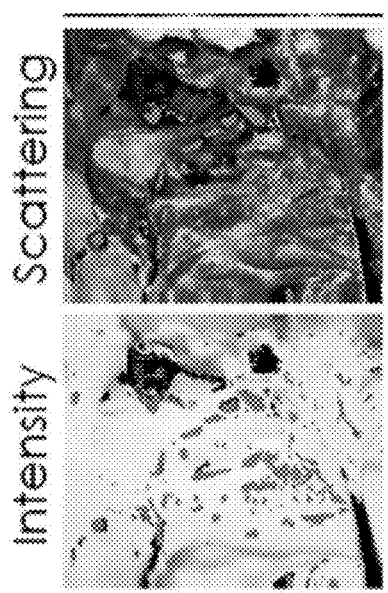
FIG. 7A Saturation
FIG. 7B Hemoglobin
FIG. 7C Fat
FIG. 7D Water
FIG. 7E Intensity
FIG. 7F Scattering

DETERMINING CHROMOPHORE CONCENTRATIONS IN TISSUES

CROSS-REFERENCE TO RELATED APPLICATIONS

This application is a continuation of U.S. patent application Ser. No. 17/311,300, filed Jun. 4, 2021, which is a U.S. National Stage Application under 35 U.S.C. § 371 of International Application No. PCT/US2019/064542, filed Dec. 4, 2019, which claims the benefit of U.S. Provisional Application No. 62/775,463, filed Dec. 5, 2018, each of which is incorporated herein by reference in its entirety.

TECHNICAL FIELD

This disclosure relates to imaging used in endoscopic surgical systems.

BACKGROUND

Minimally invasive surgical systems are being developed to reduce the trauma experienced by patients undergoing surgical interventions. These systems require only small incisions and surgeons use stick like cameras and instruments to perform the procedure. In addition to reducing trauma, teleoperated systems of this type increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site through a display device. Based on visual feedback received through the display device, the surgeon performs the surgical procedures on the patient by manipulating master control input devices, which in turn control the motion of tele-robotic instruments.

SUMMARY

In one aspect, this document features a method of presenting feedback on a state of a surgical scene being operated at using a surgical device. The method includes obtaining, using an endoscopic camera, a plurality of images of the surgical scene, each image in the plurality of images being obtained under illumination by electromagnetic radiation in a corresponding wavelength range. The corresponding wavelength ranges are selected in accordance with a set of chromophores present in the surgical scene, and any two of the corresponding wavelength ranges are at least partially non-overlapping. The method also includes determining, based on the plurality of images, a concentration of each of one or more chromophores in the set at various portions of the surgical scene, and generating, by one or more processing devices, based on information about the concentration of each of the one or more chromophores, a representation of the surgical scene. The method further includes presenting the representation of the surgical scene on an output device associated with the surgical device.

In another aspect, this document features an imaging system for presenting feedback on a state of a surgical scene being operated at using a surgical device. The system includes an endoscopic camera that obtains a plurality of images of the surgical scene, each image in the plurality of images being obtained under illumination by electromagnetic radiation in a corresponding wavelength range. The corresponding wavelength ranges are selected in accordance with a set of chromophores present in the surgical scene, wherein any two of the corresponding wavelength ranges are at least partially non-overlapping. The system also includes one or more processing devices configured to determine, based on the plurality of images, a concentration of each of one or more chromophores in the set at various portions of the surgical scene, generate, based on information about the concentration of each of the one or more chromophores, a representation of the surgical scene, and cause presentation of the representation of the surgical scene on an output device associated with the surgical device.

In another aspect, this document features one or more machine-readable storage devices having encoded thereon computer readable instructions for causing one or more processing devices to perform various operations. The operations include obtaining, from an endoscopic camera, a plurality of images of the surgical scene, each image in the plurality of images being obtained under illumination by electromagnetic radiation in a corresponding wavelength range. The corresponding wavelength ranges are selected in accordance with a set of chromophores present in the surgical scene, wherein any two of the corresponding wavelength ranges are at least partially non-overlapping. The operations also include determining, based on the plurality of images, a concentration of each of one or more chromophores in the set at various portions of the surgical scene, generating, based on information about the concentration of each of the one or more chromophores, a representation of the surgical scene, and causing presentation of the representation of the surgical scene on an output device associated with the surgical device.

Implementations of the above aspects can include one or more of the following features.

Determining the concentration of each of the one or more chromophores can include identifying a set of pixel values across multiple images in the plurality of images, wherein each pixel value in the set represents substantially a particular portion of the surgical scene, and determining, based on a chromophore model, the concentration of each of the one or more chromophores corresponding to the set of pixel values across the multiple images. The chromophore model represents relationships between combinations of pixel values and chromophore concentrations. The chromophore model can be pre-computed and stored in the form of a look-up table on a storage device accessible to the one or more processing devices. In some cases, a set of pixel values can be identified across multiple images in the plurality of images, wherein each pixel value in the set represents substantially a particular portion of the surgical scene. A determination may be made that the set of pixel values do not represent a valid concentration for at least one of the one or more chromophores, as per a chromophore model representing relationships between combinations of pixel values and chromophore concentrations, and in response, an alert indicative of a potential presence of a foreign body at the surgical scene can be generated. The corresponding wavelength ranges can be selected based on information on absorption spectra of the chromophores in the set of chromophores. The set of chromophores can include hemoglobin, oxygenated hemoglobin, fat, and water. Generating the representation of the surgical scene can include predicting a hyperspectral image of the surgical scene based on the information about the concentration of each of the one or more chromophores. The hyperspectral image can include information corresponding to wavelengths outside the wavelength ranges corresponding to the plurality of images. Generating the representation of the surgical scene can include generating a colored visible-range image of the surgical scene based on the information about the concentration of each of the one or more chromophores, the colored visible-range image representing an appearance of the surgical scene under illumination by visible light. The endoscopic camera can include fewer than three image sensors per pixel. Generating the representation of the surgical scene can include generating a narrow-band image of the surgical scene based on the information about the concentration of each of the one or more chromophores, the narrow-band image representing an appearance of the surgical scene under illumination by light outside the wavelength ranges corresponding to the plurality of images. An amount of illumination incident on the surgical scene can be estimated for illumination under one or more of the wavelength ranges corresponding to the plurality of images. An exposure time for the endoscopic camera can be adjusted based on information on the amount of illumination incident on the surgical scene. A tone-mapping operation can be performed on one or more of the plurality of images based on information on the amount of illumination incident on the surgical scene. An estimation can be made, based on at least a subset of the plurality of images, of an amount of scattering for various portions the surgical scene. Based on (i) information on the amount of scattering for various portions of the surgical scene and (ii) the information about the concentration of each of the one or more chromophores, a boundary between two different tissue types at the surgical scene can be determined. Based on (i) information on the amount of scattering for various portions of the surgical scene and (ii) the information about the concentration of each of the one or more chromophores, a boundary of a diseased portion of a tissue at the surgical scene can be determined. Based on (i) information on the amount of scattering for various portions of the surgical scene and (ii) the information about the concentration of each of the one or more chromophores, a one or more tissue types present at the surgical scene can be identified. The endoscopic camera can be configured to capture the plurality of images without a physical contact with the surgical scene. User-input can be received responsive to presenting the representation of the surgical scene on the display device, wherein the user-input pertains to operating the surgical device at the surgical scene. The camera can be disposed in the surgical device. The representation of the surgical scene can include a visual representation, and the output device comprises a display device.

Some or all of the embodiments described herein may provide one or more of the following advantages. By selecting illumination wavelength ranges in accordance with chromophores expected to be present at a surgical scene, the concentration of the chromophores at the surgical scene can be estimated from a small number of images. The chromophore estimates thus obtained can be used to predict/estimate/generate various types of feedback information about the surgical scene. For example, the chromophore concentration data can be used for accurately predicting a hyperspectral visualization of the surgical scene. In some cases, the chromophore concentration data can be used for generating other representations (e.g., a visual image, a narrow band image etc.). The representations in these modalities may be generated potentially using less complex hardware (e.g., fewer number of image sensors per pixel, less complex circuitry) and/or lower bandwidth than that would otherwise be required. In some cases, the information encoded within the above modalities may also be directly obtained from the chromophore concentration data. In some cases, by detecting aberrations in the combination of chromophore concentrations, the detection of presence of foreign bodies (e.g., metallic objects or other non-tissue material) or diseased cells/tissues may be improved.

BRIEF DESCRIPTION OF THE DRAWINGS

FIGS. 7A-7F are examples of images obtained under illumination by a set of selected wavelength ranges.

DETAILED DESCRIPTION

Figure 2:
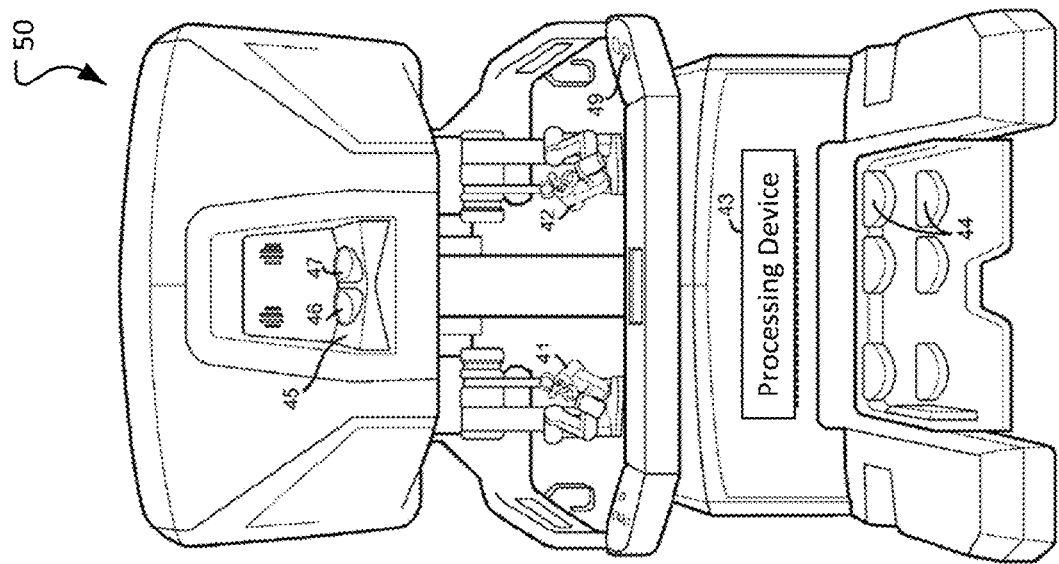
FIG. 2 is a front view of an example surgeon console of a computer-assisted tele-operated surgery system.

This document describes technology that allows for evaluating a surgical scene based on concentrations of multiple chromophores at the scene, as estimated from a set of images captured under a selected set of wavelength ranges. The set of wavelength ranges are selected based on absorption characteristics of the chromophores that are expected to be present at the surgical scene. The concentration of each of the multiple chromophores at the surgical scene, possibly over a period of time, can then be calculated based on a pre-computed model that links pixel values of the set of images with concentration of different chromophores. The chromophore concentration data thus obtained can then be used for various purposes, including, for example, estimating a representation of a hyperspectral, visible-range, or narrowband image, detecting the possible presence of foreign objects and/or diseases cells/tissues at the surgical scene, delineating boundaries between different tissue types, or obtaining other information encoded within the chromophore concentration data. In various implementations, the technology described herein can improve robotic surgical systems, for example, by allowing for implementation of complex visualization modalities such as hyperspectral imaging while using significantly less complex hardware (e.g., fewer number of image sensors per pixel, less complex circuitry) and/or lower bandwidth than that would otherwise be required. In some implementations, the visualizations and/or information afforded by the chromophore concentration data can provide for improved detection of boundaries between tissue types, identification of diseased cells/tissues, and/or identification of foreign objects (e.g., surgical tools etc.) at the surgical scene.

Aspects of the technology are described primarily in terms of an implementation using da Vinci® surgical systems developed by Intuitive Surgical, Inc. of Sunnyvale, California. Examples of such surgical systems are the da Vinci® Xi™ Surgical System (Model IS4000). It should be understood that aspects disclosed herein may be embodied and implemented in various ways, including computer-assisted, non-computer-assisted, and hybrid combinations of manual and computer-assisted embodiments and implementations. Implementations on da Vinci® Surgical Systems, e.g. the Model IS4000 are described for illustrative purposes, and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices. While the technology is described primarily with reference to an example of a peer-in display, the technology may also be used in other types of wearable or non-wearable display devices such as a head-mounted display device used, for example, in virtual or augmented reality (VR/AR) systems. The images captured may also be displayed on a large format display such as a 3D TV like device or an image projected onto a screen of some kind and viewed by a user wearing glasses that complete the stereo effect by ensuring that the correct image goes to the correct eye. Alternatively, an auto-stereo type display may be used, for example, a lenticular based LCD type of display that may also incorporate head and or eye tracking of the viewer (user).

Figure 1:
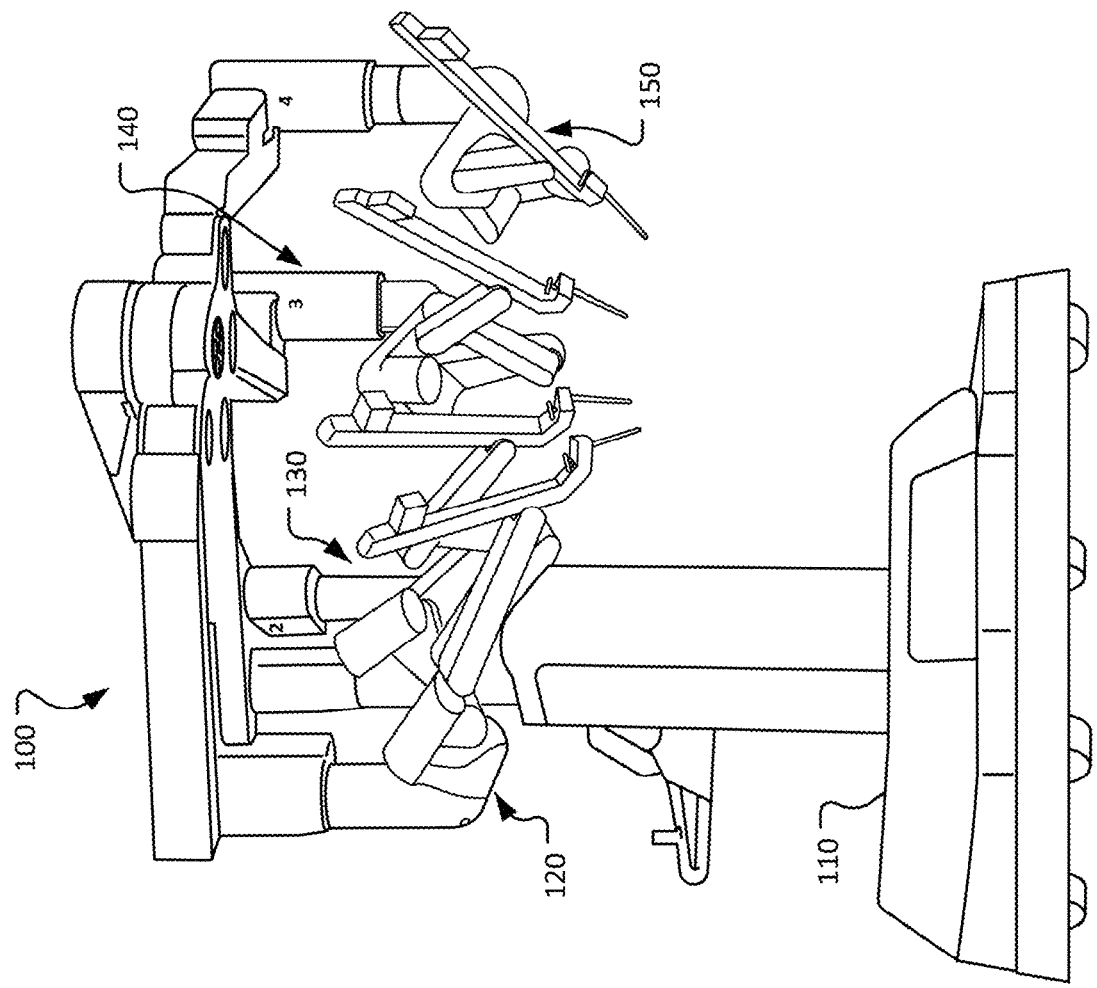
FIG. 1 is a perspective view of an example patient-side cart of a computer-assisted tele-operated surgery system.

Referring to FIGS. 1 and 2, systems for minimally invasive computer-assisted telesurgery (also referred to as MIS) can include a patient-side cart 100 and a surgeon console 50. Telesurgery is a general term for surgical systems where the surgeon uses some form of remote control, e.g., a servo-mechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient body, avoiding the trauma associated with rather large incisions required for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment, the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that a third instrument may be introduced at the work site. Alternatively, the remaining robotic manipulator arm assembly may be used for introducing a second endoscope or another image-capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 50 includes a stereoscopic peer-in display 45 so that the user may view the surgical work site in stereo vision from images captured by the stereoscopic camera used in conjunction with the patient-side cart 100. Left and right eyepieces, 46 and 47, are provided in the stereoscopic peer-in display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 50 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six or more degrees-of-freedom ("DOF"). Foot pedals 44 with toe and heel controls are provided on the surgeon console 50 so the user may control movement and/or actuation of devices associated with the foot pedals.

A processing device 43 is provided in the surgeon console 50 for control and other purposes. The processing device 43 performs various functions in the medical robotic system. One function performed by processing device 43 is to translate and transfer the mechanical motion of input devices 41, 42 to actuate their corresponding joints in their associated robotic manipulator arm assemblies 120, 130, 140, and 150 so that the surgeon can effectively manipulate devices, such as the surgical instruments. Another function of the processing device 43 is to implement the methods, cross-coupling control logic, and controllers described herein.

The processing device 43 can include one or more processors, digital signal processors (DSPs), field-programmable gate arrays (FPGAs), and/or microcontrollers, and may be implemented as a combination of hardware, software and/or firmware. In addition, its functions as described herein may be performed by one unit or divided up among a number of subunits, each of which may be implemented in turn by any combination of hardware, software and firmware. Further, although being shown as part of or being physically adjacent to the surgeon console 50, the processing device 43 may also be distributed as subunits throughout the telesurgery system. One or more of the subunits may be physically remote (e.g., located on a remote server) to the telesurgery system.

Figure 3:
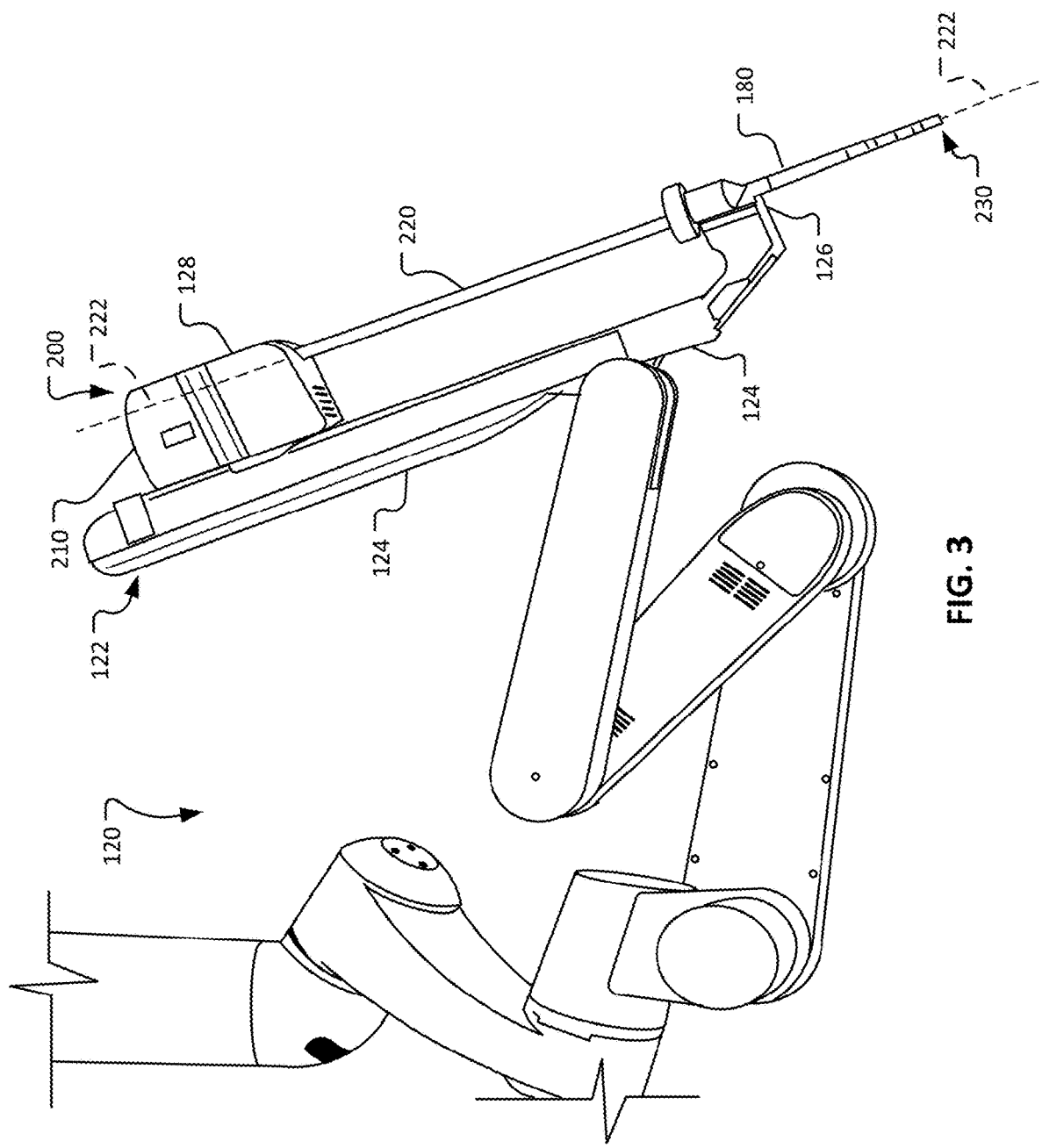
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as an endoscopic stereo camera and surgical instruments to perform minimally invasive surgery. For example, in the depicted arrangement the robotic manipulator arm assembly 120 is pivotably coupled to an instrument holder 122. A cannula 180 and a surgical instrument 200 are, in turn, releasably coupled to the instrument holder 122. The cannula 180 is a hollow tubular member that is located at the patient interface site during a surgery. The cannula 180 defines a lumen in which an elongated shaft 220 of the endoscopic camera (or endoscope) or surgical instrument 200 is slidably disposed. As described further below, in some embodiments the cannula 180 includes a distal end portion with a body wall retractor member. The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 50 using the processing device 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processing device 43. The surgical instrument 200 includes a transmission assembly 210, the elongated shaft 220, and an end effector 230. The transmission assembly 210 may be releasably coupled with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongated shaft 220 of the surgical instrument 200 is moved along the longitudinal axis 222. In such a manner, the end effector 230 can be inserted and/or retracted from a surgical workspace within the body of a patient.

Laparoscopic surgery can entail the surgeon viewing the surgical site with the endoscope and performing fine motor manipulations with laparoscopic instruments for exploration, dissection, suturing, and other surgical tasks. These tasks often require fine bi-manual interactions with tissue. In some cases, such bi-manual motor tasks may generally be more easily performed when the surgeon is presented with a 3D view of the surgical scene. The surgical workspace within the body of a patient (the surgical scene) can be presented as a 3D visualization to the surgeon via the stereoscopic display 45. While the technology described herein primarily uses examples of a peer-in stereoscopic display, other types of stereoscopic and non-stereoscopic displays are also within the scope of the technology. A peer-in stereoscopic display refers to a display that allows a user to look into the display without having to wear it or simultaneously share it with another user. A stereo microscope can be an example of a peer-in stereoscopic display. The stereoscopic display 45, as illustrated in FIG. 2 is another example of a peer-in stereoscopic display.

A chromophore is a group of atoms or electrons (also referred to as a moiety) in an organic molecule that is responsible for the color of the organic molecule. Color is manifested when a molecule absorbs certain wavelengths of electromagnetic energy (e.g., visible light) and transmits or reflects other wavelengths. A chromophore reacts to incident electromagnetic radiation in a given wavelength range if the energy of the incident electromagnetic radiation is sufficient to overcome the difference between two different molecular orbitals of the chromophore. When electromagnetic radiation in that wavelength range hits the chromophore, the corresponding energy can excite an electron from a ground into an excited state. The radiation in the corresponding wavelength is thus substantially absorbed, thereby changing the composition of the wavelength ranges of light reflected from the molecule.

Figure 4:
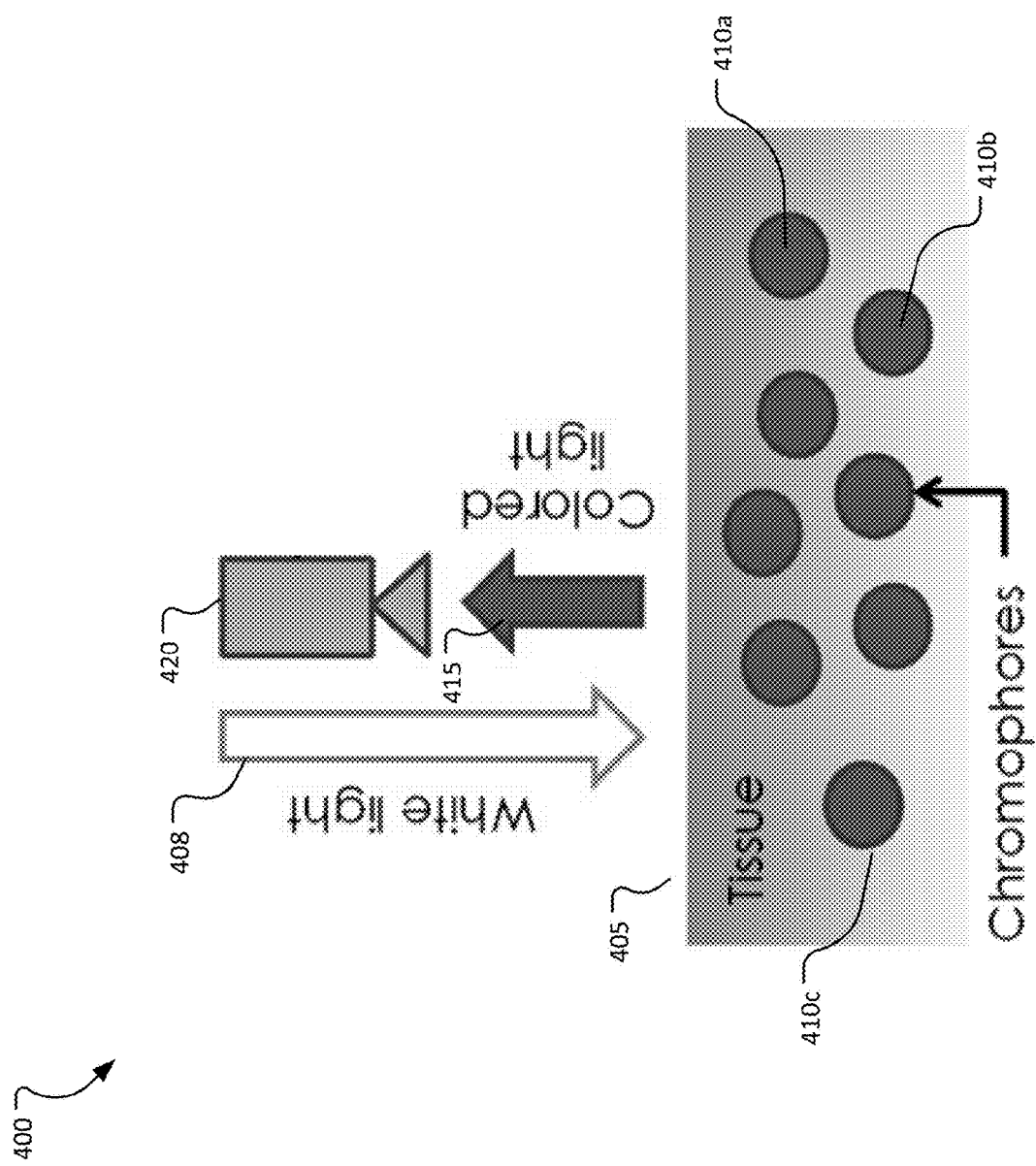
FIG. 4 is a schematic diagram illustrating the effects of chromophores on imaging of a surgical scene under white light.

FIG. 4 is a schematic diagram illustrating the effects of chromophores on imaging of a surgical scene under white light. In this example, a tissue at the surgical scene 405 is irradiated with broadband white light 408. Chromophores 410a, 410b, 410c etc. (410, in general) absorb energy corresponding to some wavelength ranges in the white light, thereby changing the composition of the wavelength ranges in the reflected light 415, potentially making the reflected light 415 appear as "colored." The reflected light 415 is sensed by an imaging device 420 (e.g., a camera), and a visual representation of the surgical scene 405 can then be generated from the information captured using the imaging device. Note that even though a chromophore is a moiety that causes a structural change in a particular molecule when hit by electromagnetic radiation, the term chromophore, as used in this document, refers to the underlying molecule itself. For instance, hemoglobin, oxygenated hemoglobin, fat, and water are used as examples of chromophores throughout this document.

Because each type of chromophore at the surgical scene 405 has a characteristic color signature, the absorption of incident light 408, and consequently the wavelength composition of the reflected light 415, depends of the concentration of various chromophores at the surgical scene 405. For example, electromagnetic radiation in the range 500-600 nm is absorbed by oxygenated hemoglobin (also referred to in shorthand as $HbO_2$) significantly more than what is absorbed by fat tissues. Therefore, the wavelength composition of the reflected light 415 due to a higher concentration of $HbO_2$ is different from the wavelength composition of the reflected light 415 due to a higher concentration of fat. Therefore, when the surgical scene is imaged under illumination by electromagnetic radiation in different wavelength ranges, the chromophores at the scene 405 affect the images differently. This document describes technology using which the concentrations of different chromophores at the surgical scene can be estimated based on the different appearances of the same region in multiple images obtained under varying illumination conditions. The number of different illumination wavelength ranges (and consequently the minimum number of images) can be dependent on the number of chromophores that are expected to be present at the surgical scene. For example, a typical surgical scene may be evaluated based on chromophore concentrations corresponding to four different chromophores—hemoglobin, oxygenated hemoglobin, fat, and water—and consequently, images may be obtained under illumination by electromagnetic radiation in four separate wavelength ranges.

Figure 5:
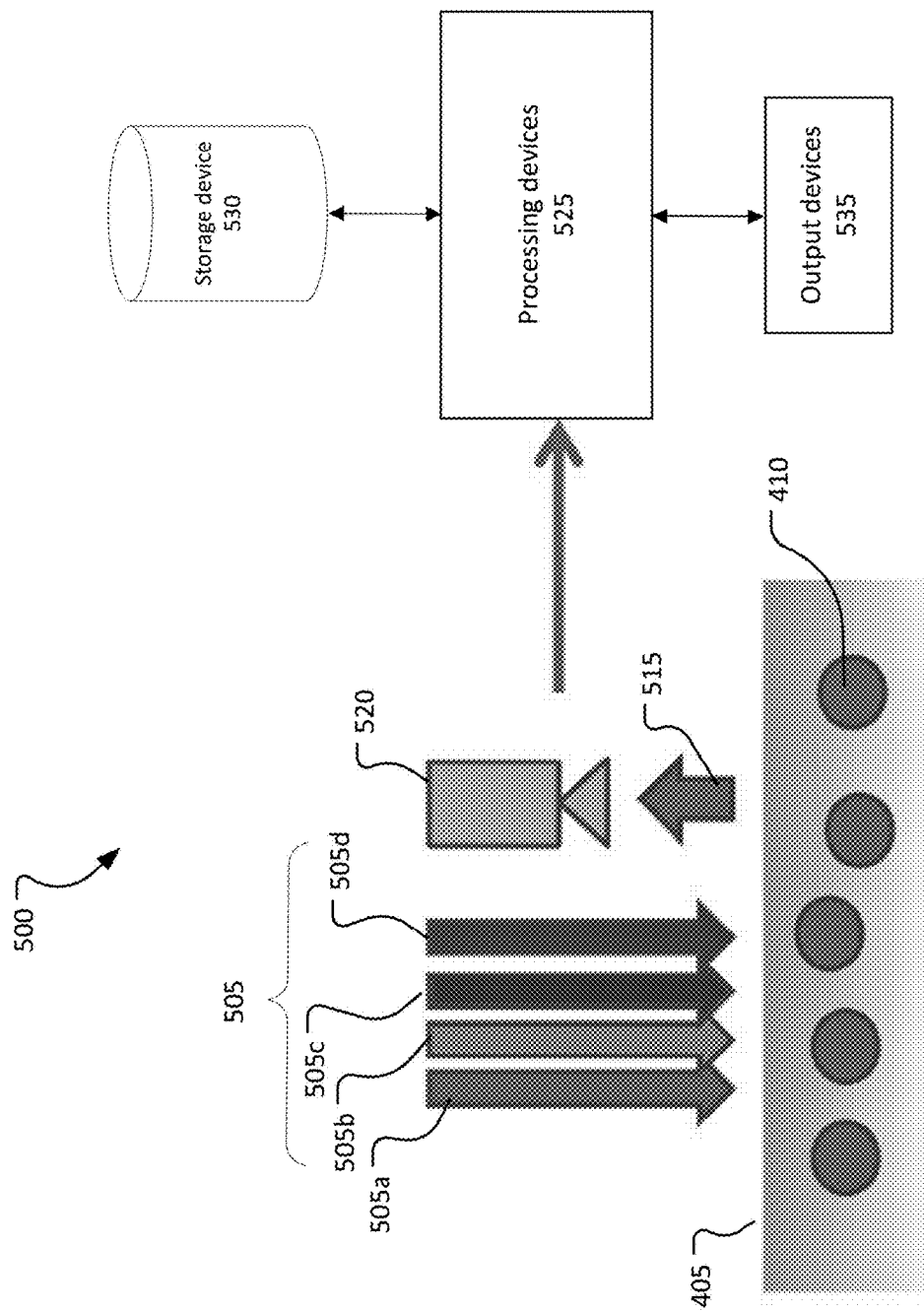
FIG. 5 is a schematic diagram illustrating chromophore imaging under illumination by a set of wavelength ranges selected in accordance with chromophores expected to be present at the surgical scene.

FIG. 5 is a schematic diagram illustrating chromophore imaging under illumination by a set of wavelength ranges selected in accordance with chromophores expected to be present at the surgical scene. In the system 500 illustrated in FIG. 5, the surgical scene 405 is illuminated by electromagnetic radiation in different wavelength ranges 505a, 505b, 505c, and 505d (505, in general), and the corresponding reflected light 515 is captured using an imaging device 520. In some implementations, the surgical scene 405 is sequentially illuminated by electromagnetic radiation in the different wavelength ranges 505, and the corresponding images captured one after another. In some implementations, the electromagnetic radiation in the different wavelength ranges 505 may be irradiated on the surgical scene substantially simultaneously, and the corresponding images captured at the imaging device 520 using corresponding optical filters. For example, the imaging device 520 can have four image sensors per pixel, each image sensor being behind an optical filter that passes light corresponding to one illumination wavelength range, but substantially blocks light corresponding to the other three illumination wavelength ranges. The example shown in FIG. 5 shows four different wavelength ranges corresponding to four chromophores, hemoglobin, oxygenated hemoglobin, fat, and water. However, more or fewer number of wavelength ranges are also within the scope of this disclosure.

Figure 6:
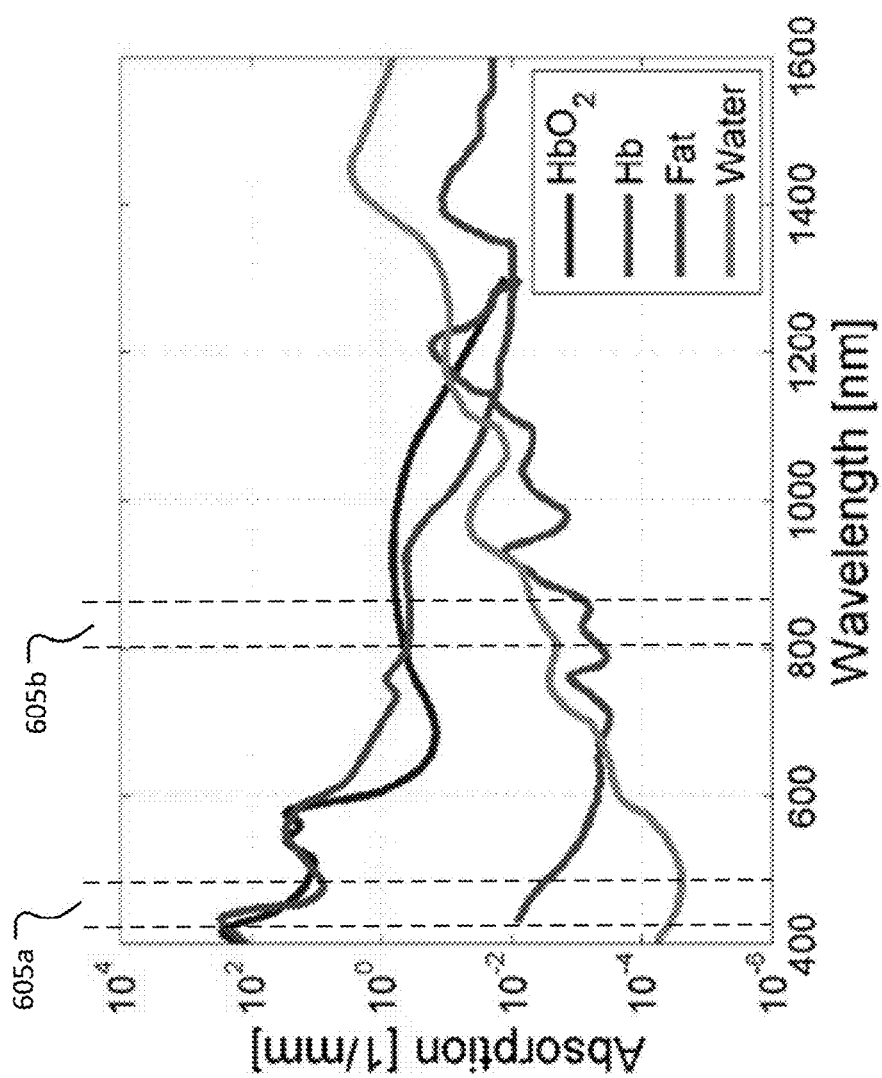
FIG. 6 is a plot showing absorption characteristics for a set of chromophores.

The illumination wavelength ranges 505 can be selected based on optical characteristics of the chromophores expected to be present at the surgical scene. In some implementations, the wavelength ranges 505 can be selected based on absorption characteristics of different chromophores, as illustrated in the example of FIG. 6. Specifically, FIG. 6 is a plot showing absorption characteristics for a set of chromophores that include hemoglobin, oxygenated hemoglobin, fat, and water. In this example, water and fat are shown to exhibit low absorption (and therefore high reflectance) for electromagnetic energy in the wavelength range 605a, as compared to hemoglobin and oxygenated hemoglobin. Also, in the wavelength range 605a, fat exhibits a higher absorption (and therefore lower reflectance) than water. In the wavelength range 605b, fat exhibits a lower absorption (and therefore higher reflectance) than water, while each of water and fat exhibits higher reflectance than hemoglobin and oxygenated hemoglobin. Therefore, images obtained under illumination ranges 605a and 605b can be expected to predominantly represent reflectance due to water and fat, respectively. Two other wavelength ranges corresponding to hemoglobin and oxygenated hemoglobin can be determined similarly from the absorption characteristics shown in FIG. 6, or based on one or more other optical characteristics. In some implementations, an illumination wavelength range can be selected such that the effect of the illumination on a corresponding chromophore of interest is substantially different from the effect on the other chromophores of interest.

Referring back to FIG. 5, the imaging device 520 is configured to obtain a separate image under illumination by each of the different wavelength ranges 505. In the example of FIG. 5, four separate wavelength ranges 505a, 505b, 505c, and 505d, and correspondingly, four separate images are obtained. In some implementations, each of the obtained images can correspond to a separate chromophore of interest. FIGS. 7A-7D show examples of such images, with these particular examples showing distribution of oxygenated hemoglobin (also, referred to as saturation, FIG. 7A), hemoglobin (FIG. 7B), fat (FIG. 7C), and water (FIG. 7D) at the surgical scene. In some implementations, one or more additional images may be derived from the captured images. For example, FIG. 7E shows an intensity image which represents the amount of electromagnetic energy incident on the corresponding area of the tissue, and FIG. 7F shows the scattering coefficients corresponding to the different portions of the surgical scene.

In some implementations, the concentration of individual chromophores at the surgical scene can be determined based on pixel values in the multiple images captured under different illumination wavelength ranges and/or the one or more images derived from such captured images. In some implementations, this can be done based on a chromophore model that represents relationships between combinations of pixel values and chromophore concentrations. For example, known concentrations of the chromophores of interest can be imaged in an offline process using substantially the same wavelength ranges to generate sets of training images. A look-up table can then be created from the set of training images, the look-up table storing the concentration values of chromophores linked to the combination of pixel values from the multiple images. For example, assuming that the examples images of FIGS. 7A-7F are training images, and a pixel at location $(x_1, y_1)$ in each of the six images represents a same location of the tissue. If the concentration of the four chromophores—oxygenated hemoglobin, hemoglobin, fat, and water—at that location are known to be $C_1$, $C_2$, $C_3$, and $C_4$, respectively, the six dimensional n-tuple $(p_1, p_2, p_3, p_4, p_5, p_6)$ representing pixel value from each of the six images can be stored in a lookup table as linked to the four dimensional n-tuple $(C_1, C_2, C_3, C_4)$ representing the corresponding chromophore concentrations. Based on multiple sets of training images, various combinations of chromophore concentration can be linked to corresponding n-tuples of pixel values. Referring back to FIG. 5, such a lookup table can be stored in a storage device 530 accessible to one or more processing devices 525. In some implementations, the one or more processing devices 525 can be provided as a part of the processing device 43 described with reference to FIG. 2.

During runtime, the one or more processing devices 525 can be configured to analyze the multiple images captured by the imaging device 520 to determine the chromophore concentrations in the underlying tissue. For example, the one or more processing devices can be configured to extract, from each of the multiple images, a pixel value that represents the same underlying portion of the tissue, to obtain an ordered combination of pixel values. The processing devices 525 can then parse the look-up table to identify an n-tuple of pixel values that substantially match the ordered combination of pixel values extracted from the multiple images, and extract the corresponding n-tuple of chromophore concentrations to obtain the concentrations of the different chromophores estimated to be present in the underlying portion of the tissue. The process can be repeated for other pixel values in the multiple images to obtain a map of the chromophore concentrations in the underlying tissue.

In some implementations, the n-tuples representing pixel values from multiple images can be determined using an analytical model representing relationships between chromophore concentrations and corresponding reflectance (which in turn is indicative of pixel values). For example, an analytical model that may be used is represented as:

$$R(\lambda, x) = I_0(x) * \Sigma_d p(d) * e^{(-u_a(\lambda, x) * d)} \qquad (1)$$

where R(λ, x) represents reflectance Δ due to a chromophore x, $I_0(x)$ represents incident light intensity, $u_a(\lambda, x)$ represents the corresponding absorption spectra value, p(d) represents the probability that the chromophore x is at a depth d. The absorption spectra value can be determined as:

$$u_a(\lambda, x) = u_{a\text{-}model} * w(x) \quad (2)$$

wherein w(x) represents concentration of the chromophore x. The depth probability p(d) is determined as:

$$p(d) = e^{-u_s(\lambda, x) * d} \quad (3)$$

wherein $u_s(\lambda, x)$ is the scattering spectra value that may be obtained as:

$$u_s(\lambda, x) = (\lambda/500)^{-b(x)} \quad (4)$$

wherein b(x) represents the Mie scattering coefficient. In some implementations, this analytical model can be used to generate pixel values for the different values of concentration for different chromophores. In some implementations, the generated values may be stored as a look-up table as described above.

The chromophore concentration determined by analyzing images captured under illumination by a limited set of wavelength ranges can be used in various ways. In some implementations, the concentration data corresponding to individual chromophores can be used for various diagnostic and visualization purposes. For example, the distribution of oxygenated hemoglobin (as illustrated, for example using the saturation map of FIG. 7A) can be indicative of perfusion in tissues. Further, because perfusion can be indicative of tissue health, the saturation map may also be used for determining dead or relatively unhealthy portions of the tissue. In some implementations, the concentration data associated with hemoglobin (e.g., as illustrated in FIG. 7B), fat (e.g., as illustrated in FIG. 7C), or water (as illustrated in FIG. 7D) can be used to delineate boundaries between different tissue types. In some implementations, the concentration data associated with hemoglobin can be used for determining adhesion in tissues. In some implementations, one or more of the derived images can also be used for diagnostic and/or visualization purposes. For example, a scattering map (e.g., as illustrated in FIG. 7F) may be used for identifying locations of diseased cells/tissues such as cancer. In another example, the intensity map (e.g., as illustrated in FIG. 7E) can be used to inform whether better exposure and/or dynamic contrast would be useful in obtaining the images.

Referring back to FIG. 5, the chromophore concentration data can be processed by the one or more processing devices 525 to generate control signals for one or more output devices 535. In some implementations, the output devices 535 can include a display device (e.g., the stereoscopic display 45), and chromophore data can be rendered as an image on the display device. In some implementations, the information encoded within the image data associated with the chromophore concentrations, may be directly extracted and presented on the output device 535. For example, the one or more processing devices 525 can be configured to process the chromophore data to determine that an extracted n-tuple of pixel values do not correspond to any valid combination of chromophore concentrations. In such a case, the one or more processing devices can be configured to determine that the non-conforming n-tuple results from the presence of a non-tissue foreign object at the surgical scene. Responsive to such determination, the one or more processing devices 525 can be configured to generate an alert (e.g., an audible or visible alarm), possibly in addition to displaying any images on a display device. The technology described herein can therefore potentially be used for improving safety of a surgical procedure by improving foreign body detection capabilities of a surgical system.

Figure 8:
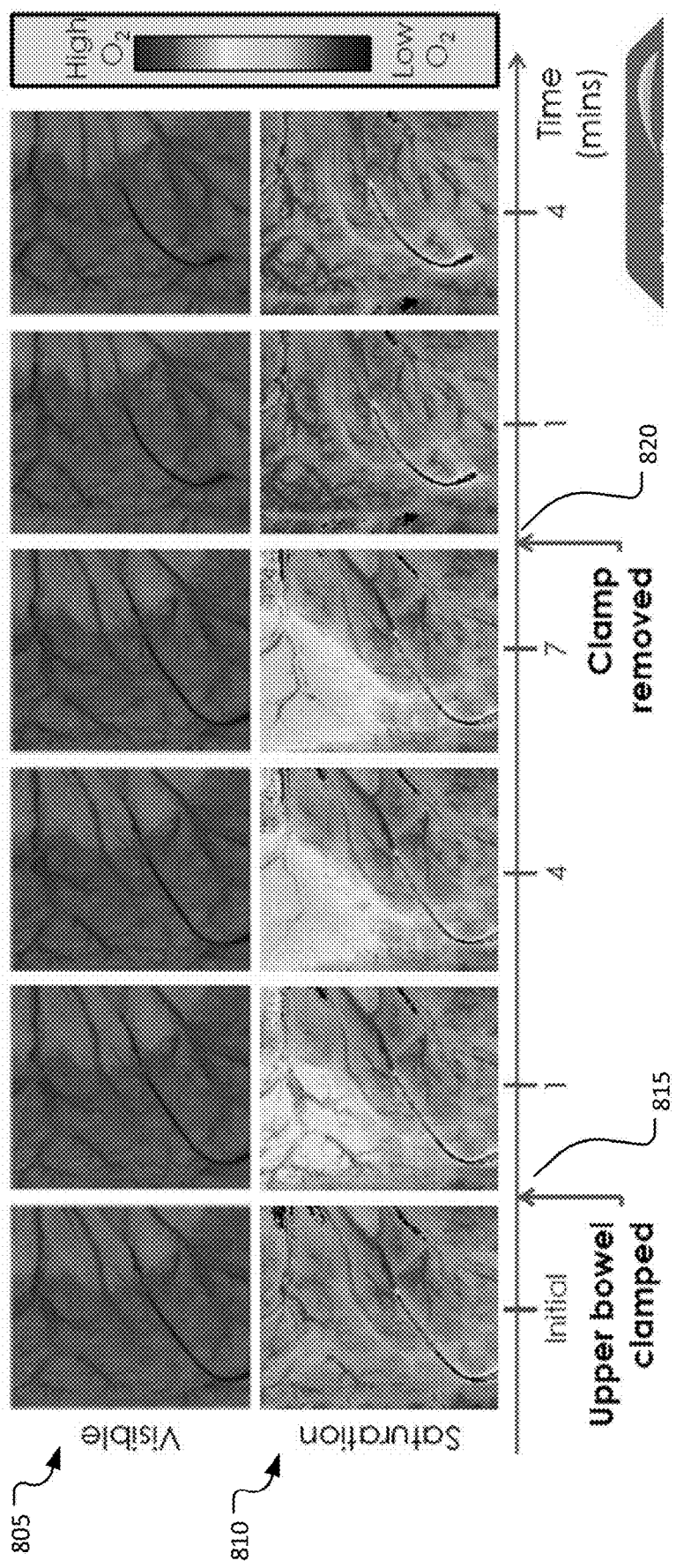
FIG. 8 is a set of images illustrating an example of variation over time in concentration of an example chromophore—oxygenated hemoglobin—at a surgical scene.

In some implementations, the chromophore concentration data may improve visualization of the tissue during a surgical procedure, for example, by allowing for display of information that is not available in regular images obtained under illumination by light in the visible range. This is illustrated using FIG. 8, which shows a set of images illustrating an example of variation over time in concentration of an example chromophore—oxygenated hemoglobin—at a surgical scene. The top row 805 shows a set of images of a portion of a human bowel, as captured sequentially over a period of time. The bottom row 810 shows corresponding saturation images (as generated from concentration data associated with oxygenated hemoglobin) obtained at the same points of time. During the time period over which the images were captured, a clamp was placed at an upper portion of the bowel at time 815, and then removed at time 820. The sequence of images between the two time points 815 and 820 on row 810 show that the oxygenated hemoglobin concentration decreased in a portion of the tissue (which is expected due to clamping of blood flow into the tissue), and then increased again after removal of the clamp. The visible-range images (as seen in row 805) remains substantially unchanged during this time period, which illustrates the value of the information in the images generated from the chromophore data.

Figure 9:
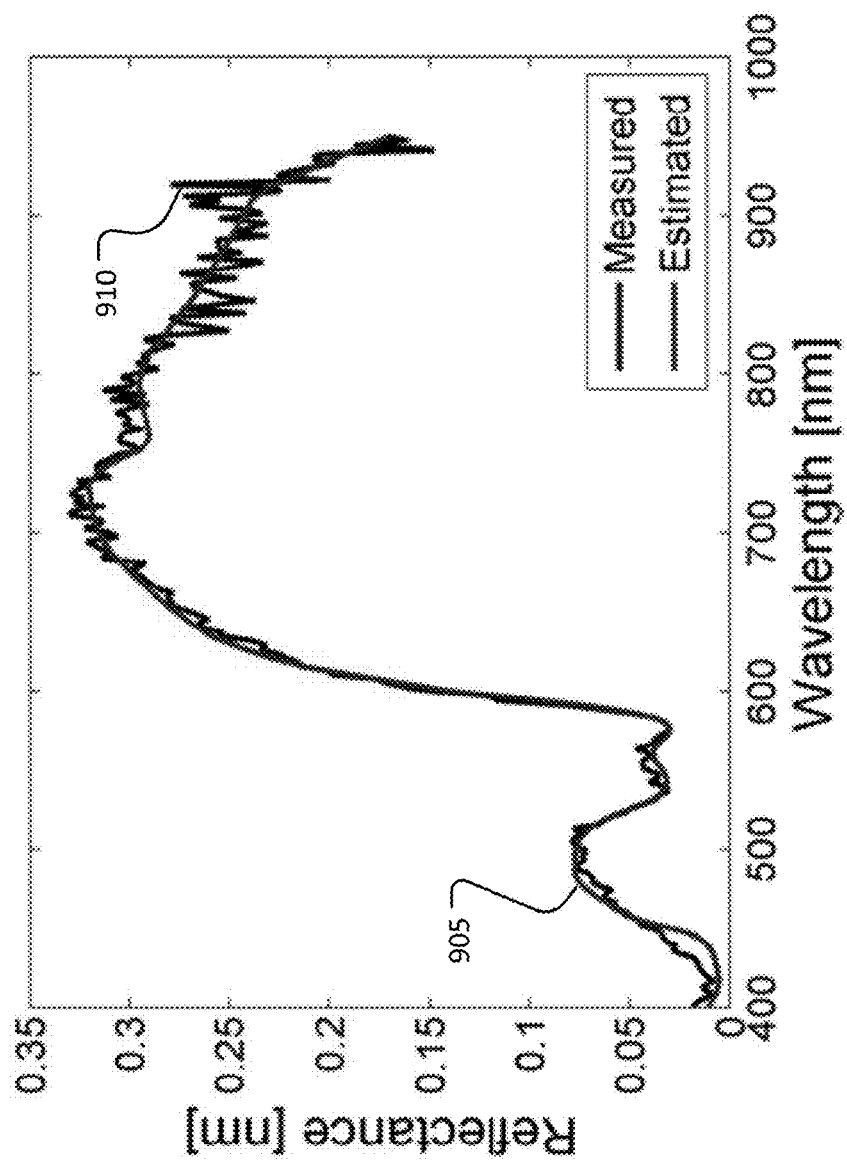
FIG. 9 is an example plot showing comparisons between reflectance characteristics associated with an actual hyperspectral image of a surgical scene and that associated with a hyperspectral image predicted from chromophore concentration data of the same surgical scene.

In some implementations, the chromophore data generated by illuminating the tissue with electromagnetic radiation in a small number of wavelength ranges can be used to estimate information that would be available upon illumination in other wavelength ranges. The chromophore data can therefore be used for estimating/generating other wideband images such as hyperspectral images, or RGB images, and/or narrowband images such as near-infrared (NIR) images. This can be done, for example, via a look-up table that stores relationships between pixel values (or reflectance characteristics) of a wideband (or narrowband) image and corresponding combinations of chromophore concentrations. FIG. 9 is an example plot showing comparisons between reflectance characteristics associated with an actual hyperspectral image of a surgical scene and that associated with a hyperspectral image predicted from chromophore concentration data of the same surgical scene. Specifically, the curve 905 shows reflectance values predicted for a hyperspectral image over a wide frequency range, and the curve 910 shows the corresponding measured reflectance values of an actual hyperspectral image of the same tissue. Comparing the two curves 905 and 910, it can be seen that the true values of a hyperspectral image can be predicted accurately from the chromophore concentration values for most part of the spectrum.

By allowing for prediction of multiple wideband and/or narrowband images based on the same chromophore data, the technology described herein can allow for implementation of a multi-purpose camera (e.g., a camera that can be used to generate hyperspectral, visible-range, and NIR images) without incorporating any additional hardware. By reducing the hardware and/or bandwidth requirement, the technology also facilitates a multi-purpose or hyperspectral camera to be implemented within the limited real-estate of an endoscope, thereby allowing for realization of hyperspectral or multi-purpose endoscopes that significantly improve real-time visualization for surgeons, and allows for capturing images of a surgical scene or tissues without making a physical contact with the surgical scene or tissue, respectively.

Figure 10:
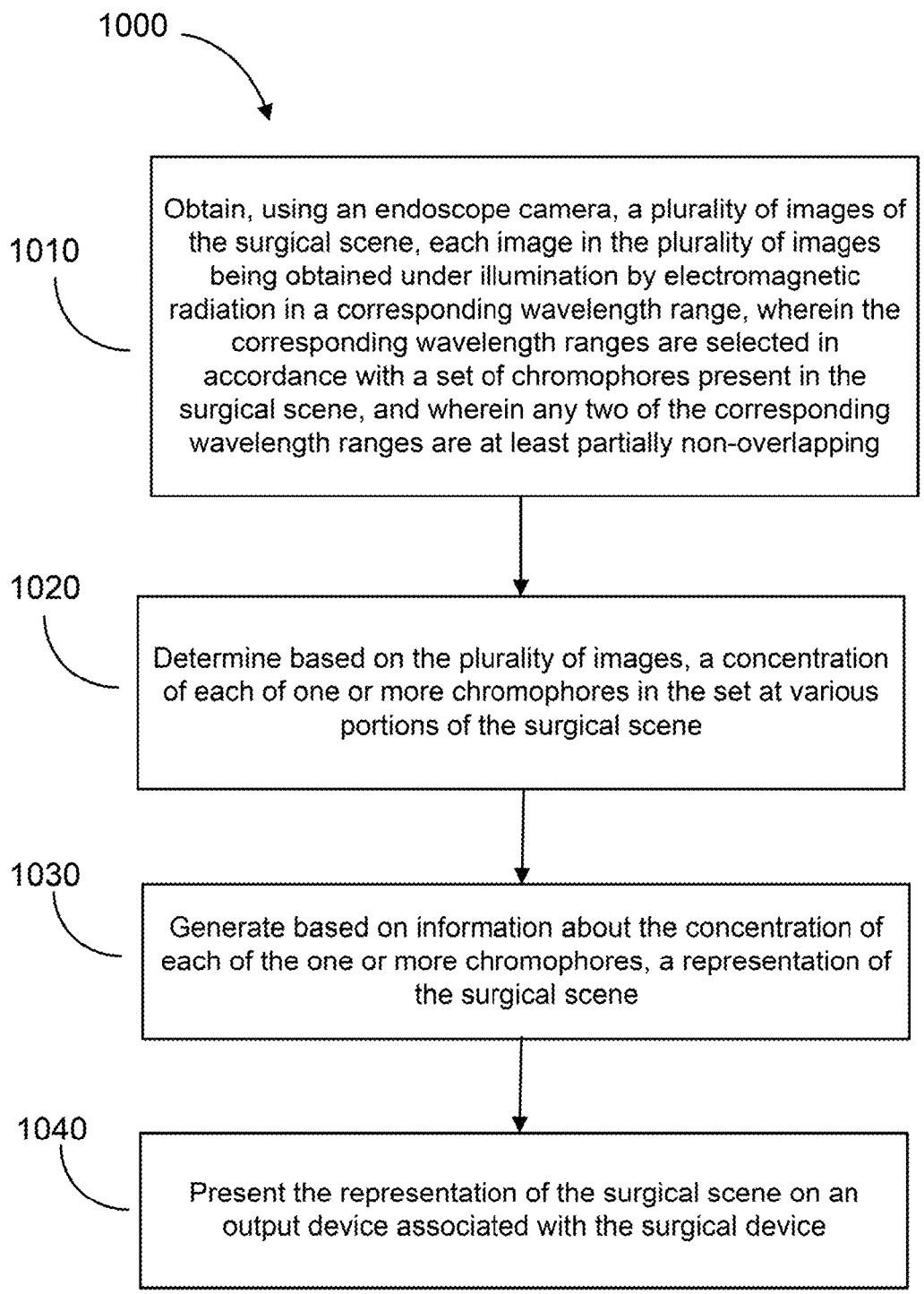
FIG. 10 is a flowchart of an example process for presenting a representation that in accordance with technology described herein.

FIG. 10 is a flowchart of an example process 1000 for presenting a representation that in accordance with technology described herein. The process 1000 can be executed, at least in part by the one or more processing devices 525 described with reference to FIG. 5. Operations of the process 1000 includes obtaining, using an endoscopic camera, a plurality of images of the surgical scene (1010). Each image in the plurality of images can be obtained under illumination by electromagnetic radiation in a corresponding wavelength range, wherein the corresponding wavelength ranges are selected in accordance with a set of chromophores present in the surgical scene. Any two of the corresponding wavelength ranges are at least partially non-overlapping. In some implementations, the corresponding wavelength ranges can be selected based on information on absorption spectra of the chromophores in the set of chromophores.

In some implementations, one or more additional images can be generated from images captured using the endoscopic camera, and included in the plurality of images. For example, an amount of illumination incident on the surgical scene can be estimated for illumination under one or more of the wavelength ranges, and a derivative image can be generated accordingly. Such an image can be used in various ways. For example, an exposure time for the endoscopic camera can be adjusted based on information on the amount of illumination incident on the surgical scene. In another example, a tone-mapping operation may be performed on one or more of the plurality of images based on information on the amount of illumination incident on the surgical scene. In some implementations, an amount of scattering for various portions the surgical scene can be estimated from one or more of the images captured using the camera, and a derivative image generated accordingly. The scattering image may be used, for example, to identify locations of cells/tissues afflicted with a disease such as cancer.

Operations of the process 1000 also includes determining, based on the plurality of images, a concentration of each of one or more chromophores in the set at various portions of the surgical scene (1020). In some implementations, this can include, for example, identifying a set of pixel values across multiple images in the plurality of images, wherein each pixel value in the set represents substantially a particular portion of the surgical scene, and determining, based on a chromophore model, the concentration of each of the one or more chromophores corresponding to the set of pixel values across the multiple images. For example, an n-tuple (or ordered combination) of pixel values corresponding to analogous pixels in the multiple images may be extracted, and the corresponding combination of chromophores can be determined from a chromophore model. In some implementations, the chromophore model represents relationships between combinations of pixel values and chromophore concentrations, and can be stored as a pre-computed look-up table, as described above. In some implementations, the chromophore model can be represented as a set of analytical equations such as equations (1)-(4) above.

Operations of the process 1000 further includes generating, based on information about the concentration of each of the one or more chromophores, a representation of the surgical scene (1030). This can include, for example, generating a colored visible-range image of the surgical scene based on the information about the concentration of each of the one or more chromophores, the colored visible-range image representing an appearance of the surgical scene under illumination by visible light. In another example, generating the representation of the surgical scene can includes generating a narrow-band image of the surgical scene based on the information about the concentration of each of the one or more chromophores. The narrow-band image can represent an appearance of the surgical scene under illumination by light outside the wavelength ranges corresponding to the plurality of images. In some implementations, generating the representation of the surgical scene includes predicting a hyperspectral image of the surgical scene based on the information about the concentration of each of the one or more chromophores, the hyperspectral image including information corresponding to wavelengths outside the wavelength ranges corresponding to the plurality of images.

The generated chromophore information may be used in multiple other ways. For example, the chromophore concentration information can be used in detecting a presence of a foreign body (or non-tissue material) at the surgical scene. This can include, for example, first identifying a set of pixel values across multiple images in the plurality of images, each pixel value in the set representing substantially a particular portion of the surgical scene. Then a determination may be made that the set of pixel values do not represent a valid concentration for at least one of the one or more chromophores, as per a chromophore model representing relationships between combinations of pixel values and chromophore concentrations. Responsive to such a determination, an alert (e.g., an audible or visible alarm) indicative of a potential presence of a foreign body at the surgical scene can be generated. In some implementations, a boundary between two different tissue types at the surgical scene can be determined based on, for example, information on the amount of scattering for various portions of the surgical scene, and the information about the concentration of each of the one or more chromophores. In some implementations, the information on the amount of scattering and the information about the concentration of each of the one or more chromophores can be used for identifying a boundary of a diseased portion of a tissue at the surgical scene, and/or a one or more tissue types present at the surgical scene.

The functionality of the tele-operated surgery system described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a microcontroller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one or more processing devices at one site or distributed across multiple sites and interconnected by a network.

Actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on what may be claimed, but rather as descriptions of features that may be specific to particular embodiments. Other embodiments may also be within the scope of the technology described herein. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

The invention claimed is:

1. A method of presenting feedback on a state of a surgical scene being operated at using a surgical device, the method comprising:
    obtaining, using an imaging device, a plurality of images of the surgical scene, each image in the plurality of images being obtained under illumination by electromagnetic radiation in one of a plurality of wavelength ranges, wherein the plurality of wavelength ranges are at least partially non-overlapping;
    identifying a set of pixel values across multiple images in the plurality of images, wherein each pixel value in the set of pixel values is substantially representative of a particular portion of the surgical scene;
    determining, based on the set of pixel values and a chromophore model, a concentration of a chromophore in the particular portion of the surgical scene, wherein the chromophore model represents relationships between combinations of pixel values and chromophore concentrations; and
    presenting, by a display device, a representation of the surgical scene, the representation generated based on information about the concentration of the chromophore.

2. The method of claim 1, wherein one or more wavelength ranges included in the plurality of wavelength ranges are selected in accordance with a set of chromophores present in the surgical scene.

3. The method of claim 1, wherein the chromophore model is pre-computed and stored in the form of a look-up table on a storage device accessible to one or more processing devices.

4. The method of claim 1, further comprising:
    determining that the set of pixel values do not represent a valid concentration for the chromophore, as per the chromophore model representing relationships between combinations of pixel values and chromophore concentrations; and
    responsive to determining that the set of pixel values do not represent a valid concentration for the chromophore, generating an alert indicative of a potential presence of a foreign body at the surgical scene.

5. The method of claim 1, wherein one or more wavelength ranges included in the plurality of wavelength ranges are selected based on information on absorption spectra of chromophores in a set of chromophores.

6. The method of claim 1, wherein the chromophore includes hemoglobin, oxygenated hemoglobin, fat, or water.

7. The method of claim 1, further comprising:
    generating, by one or more processing devices, based on information about the concentration of the chromophore, the representation of the surgical scene.

8. The method of claim 7, further comprising receiving user-input responsive to presenting the representation of the surgical scene on the display device, wherein the user-input pertains to operating a surgical device at the surgical scene.

9. The method of claim 7, wherein generating the representation of the surgical scene comprises predicting a hyperspectral image of the surgical scene based on the information about the concentration of the chromophore, the hyperspectral image including information corresponding to wavelengths outside wavelength ranges corresponding to the plurality of images.

10. The method of claim 7, wherein generating the representation of the surgical scene comprises generating a colored visible-range image of the surgical scene based on the information about the concentration of the chromophore, the colored visible-range image representing an appearance of the surgical scene under illumination by visible light.

11. The method of claim 10, wherein the imaging device is an endoscopic camera that includes fewer than three image sensors per pixel.

12. The method of claim 7, wherein generating the representation of the surgical scene comprises generating a narrow-band image of the surgical scene based on the information about the concentration of the chromophore, the narrow-band image representing an appearance of the surgical scene under illumination by light outside wavelength ranges corresponding to the plurality of images.

13. The method of claim 1, further comprising estimating an amount of illumination incident on the surgical scene for illumination under one or more wavelength ranges corresponding to the plurality of images.

14. The method of claim 1, further comprising estimating, based on at least a subset of the plurality of images, an amount of scattering for various portions the surgical scene.

15. The method of claim 14, further comprising determining, based on (i) information on the amount of scattering for various portions of the surgical scene and (ii) the information about the concentration of the chromophore, a boundary between two different tissue types at the surgical scene.

16. The method of claim 14, further comprising identifying, based on (i) information on the amount of scattering for various portions of the surgical scene and (ii) the information about the concentration of the chromophore, one or more tissue types present at the surgical scene.

17. An imaging system for presenting feedback on a state of a surgical scene being operated at using a surgical device, the system comprising:
    an imaging device that obtains a plurality of images of the surgical scene, each image in the plurality of images being obtained under illumination by electromagnetic radiation in one of a plurality of wavelength ranges, wherein the plurality of wavelength ranges are at least partially non-overlapping; and one or more processing devices configured to:
  identify a set of pixel values across multiple images in the plurality of images, wherein each pixel value in the set of pixel values is substantially representative of a particular portion of the surgical scene, and
  determine, based on the set of pixel values and a chromophore model, a concentration of a chromophore in the particular portion of the surgical scene, wherein the chromophore model represents relationships between combinations of pixel values and chromophore concentrations; and
  direct a display device to present a representation of the surgical scene, the representation generated based on information about the concentration of the chromophore.

18. The imaging system of claim 17, wherein one or more wavelength ranges included in the plurality of wavelength ranges are selected in accordance with a set of chromophores present in the surgical scene.

19. The imaging system of claim 17, wherein one or more wavelength ranges included in the plurality of wavelength ranges are selected based on information on absorption spectra of a set of chromophores.

20. One or more machine-readable storage devices having encoded thereon computer readable instructions for causing one or more processing devices to perform operations for presenting feedback on a state of a surgical scene being operated at using a surgical device, the operations comprising:

obtaining, from an imaging device, a plurality of images of the surgical scene, each image in the plurality of images being obtained under illumination by electromagnetic radiation in a plurality of wavelength ranges, wherein the plurality of wavelength ranges are at least partially non-overlapping;

identifying a set of pixel values across multiple images in the plurality of images, wherein each pixel value in the set of pixel values is substantially representative of represents a particular portion of the surgical scene, and determining, based on the set of pixel values and a chromophore model, a concentration of a chromophore in the particular portion of the surgical scene, wherein the chromophore model represents relationships between combinations of pixel values and chromophore concentrations; and instructing a display device to present a representation of the surgical scene, the representation generated based on information about the concentration of the chromophore.

* * * * *